(12) United States Patent
Lepage et al.

(10) Patent No.: US 8,018,228 B2
(45) Date of Patent: Sep. 13, 2011

(54) HIGH RESOLUTION AND FLEXIBLE EDDY CURRENT ARRAY PROBE

(75) Inventors: Benoit Lepage, Quebec (CA); Denis Faucher, Quebec (CA)

(73) Assignee: Olympus NDT, Waltham, MA (US)

( * ) Notice: Subject to any disclaimer, the term of this patent is extended or adjusted under 35 U.S.C. 154(b) by 274 days.

(21) Appl. No.: 12/483,649

(22) Filed: Jun. 12, 2009

(65) Prior Publication Data

US 2010/0007342 A1    Jan. 14, 2010

Related U.S. Application Data

(60) Provisional application No. 61/061,480, filed on Jun. 13, 2008.

(51) Int. Cl.
*G01R 33/12* (2006.01)
*G01N 27/82* (2006.01)

(52) U.S. Cl. ........ 324/240; 324/242; 324/228; 324/232; 324/262

(58) Field of Classification Search .................. 324/240, 324/242, 228, 232, 262
See application file for complete search history.

(56) References Cited

U.S. PATENT DOCUMENTS

| 4,543,528 A | 9/1985 | Baraona |
|---|---|---|
| 5,315,234 A | 5/1994 | Sutton, Jr. et al. |
| 5,659,248 A | 8/1997 | Hedengren et al. |
| 7,078,895 B1 | 7/2006 | Shoji |
| 2003/0025496 A1 | 2/2003 | Trantow et al. |

OTHER PUBLICATIONS

Search Report issued by European Patent Office in connection with corresponding application No. EP 09 16 2688 on Feb. 3, 2011.

*Primary Examiner* — Reena Aurora
(74) *Attorney, Agent, or Firm* — Ostrolenk Faber LLP (57) ABSTRACT

Disclosed is a method and an NDT/NDI probe deploying a slit or a flexible joint of probe bending region, preferably between two rows of probe elements to allow free bending between rows of probe elements and along the direction of the rows of elements and to allow two adjacent rows of elements to bend individually along its own natural bending lines perpendicular to the direction of the rows of elements. Also disclosed is the use of protective flexible pads to cover the probe elements and other probe components.

17 Claims, 7 Drawing Sheets

HIGH RESOLUTION AND FLEXIBLE EDDY CURRENT ARRAY PROBE

CROSS REFERENCE TO RELATED APPLICATIONS

The present application claims the benefit of U.S. Provisional Patent Application No. 61/061,480 filed on Jun. 13, 2008; which is incorporated herein by reference in its entirety.

FIELD OF THE INVENTION

The present invention relates to non-destructive testing and inspection devices (NDT/NDI) and more particularly to the flexibility of the probes and/or transducers of an NDT/NDI system such as eddy current array (ECA) inspection systems.

BACKGROUND OF THE INVENTION

A typical ECA probe includes a plurality of coil elements arranged side-by-side on a base of usually printed circuit board (PCB) or other plastic material. Each coil element functions as an individual eddy current sensor which is coupled via a cable or the like to a data acquisition and processing module. In a typical inspection operation, an ECA probe is moved over a surface of a body being tested, e.g. the exterior surface of a pipe, or the fuselage of an aircraft. When the probe passes over a flaw, such as a crack or the like, each coil element passing over the flaw generates a signal, the characteristics of which can be used to determine the location and the size of the flaw.

A typical ECA probe often has two rows of coils that are staggered with each other to better detect defects with an orientation parallel to scan direction.

Ideally, to detect flaws with as high a resolution as possible using an ECA probe, each coil element should follow the contour of the surface of the body under non-destructive testing. In the past, rigid probes shaped to follow the contour of a surface, have been used to obtain a close matching of the probe and the surface being tested. Such a solution, however, has been limited to a few high volume applications because it requires the probe to be custom made for the surface of the body that is to be tested. This solution is not economical for low volume applications.

Thus, there has been a need for an ECA probe that is suitable of being used in testing for a body having a surface with a varying profile in all three dimensions (referred hereinafter as a 3D-shaped surface).

Existing efforts addressing the need of matching 3D-shaped test object surfaces include flexible ECA probes. Such prior art flexible ECA probes include a flexible base. The objective of these known probes is to obtain a probe capable of conforming to a 3D-shaped surface in order to obtain as high a resolution as possible.

One limitation of a prior art flexible ECA probe is its inability to bend around more than one direction simultaneously, which may impede an operator from accurately testing an object. This limitation is particularly severe when the bending direction is transverse to one another.

Another typical problem associated with another ECA probe relates to the staggering of the different rows coils. The staggering arrangement is often required to obtain 100% scanning coverage of the surface of the test object body because each coil is generally capable of detecting a defect that is within 50% of the coil's radius. This means that the center points of coils of one row are offset from the center points of the coils of the adjacent row. As a result, the natural bending line between two coils in one row of coils runs right through the center of a coil of the adjacent row of coils. That is to say, the natural bending lines between any two elements in one row of coils are stopped or impeded by the coils of the adjacent row. As a result, the probe is prevented from bending at natural bending lines roughly perpendicular to the rows of the elements.

Thus, given that existing flexible probes can not be bent at directions roughly perpendicular to the row of coils, the bending of the probe can only be attained through the deformation of the base of the probe, which may lead to the failure of the probe.

To overcome the problem noted above, ECA probes have been proposed in which the coils are embedded in a flexible circuit board or printed on a flexible circuit board. Examples of such proposals are disclosed in U.S. Pat. Nos. 7,078,895, 7,012,425, 6,954,065, 6,545,467, 6,452,384, 6,351,120, 6,288,537, 6,114,849, 5,841,277, 5,801,532, 5,389,876, and 5,047,719. The drawbacks of these printed or embedded coils are that the number of turns in each coil is limited by the PCB fabrication. Thus, it is not possible to build efficient low frequency coils. Moreover, it is not possible to integrate ferrites or coils with a winding direction not parallel to the surface of the probe.

Yet another prior art solution exists in which coils are glued to the surface of a substrate and each is individually connected to a data cable. A probe of such design includes the following drawbacks. First it can not be bent substantially since the wiring needs to move behind the coils. Secondly it is not possible to build a reliable high resolution probe because cables tend to break. Thirdly, it is not possible to apply pressure directly behind the coils as such pressure is exerted on the unstructured cable and hence reduces the quality of the signal. Lastly, this design presents the same problem of not being able to bend across the coil row direction.

SUMMARY OF THE INVENTION

The invention disclosed herein solves the problems related to the flexibility of probes, transducers and sensors used in NDT/NDI devices such as eddy current systems where the existing non-flexible and flexible probes present the aforementioned drawbacks, such as undesirable rigidity and increased stress force within backing materials. Note that the terms "probe", "transducer", and "sensor" used herein may be used interchangeably.

Accordingly, it is a general object of the present disclosure to provide a method and an NDT/NDI probe with desirable flexibility to achieve intimate fit between the probe and the 3-D surface of test objects without causing excessive stress force to the backing of the probe.

It is further an object of the present disclosure to deploy a slit or a flexible joint on the probe backing, preferably between two rows of probe elements to allow free movement between rows of elements and along the direction of the rows of elements.

It is further an object of the present disclosure to utilize the slit or the flexible joint at the probe backing to discontinue and relieve the stress force in the backing caused by non-uniform bending from one row to another.

It is further an object of the present disclosure to use the slit or the flexible joint to allow two rows of elements to bend individually along each row's own natural bending lines roughly perpendicular to the direction of the rows of element.

It is further an object of the present disclosure to use the slit or the flexible joint to allow bending and twisting of the probe at directions roughly perpendicular to the direction of rows.

It is further an object of the present disclosure to utilize protective blocks covering coil elements, bond pads of ECA probes so that pressure on or rough handling of the probe do not affect accurate signal reading form the test.

It can be understood that the presently disclosed method and probe provide the advantages of having better fitting between the probe and a 3-D surface of test objects when the probe is moved across the 3-D surface.

It also can be understood that the presently disclosed probe provides the advantages of longer service life due to much less stress force and deformation exerted on probe backing.

In addition, one embodiment of the presently disclosed probe provides the advantage of having the probe elements and other components protected by protective pads from pressure and rough handling during test operation.

DETAILED DESCRIPTION OF PREFERRED EMBODIMENT

Figure 1:
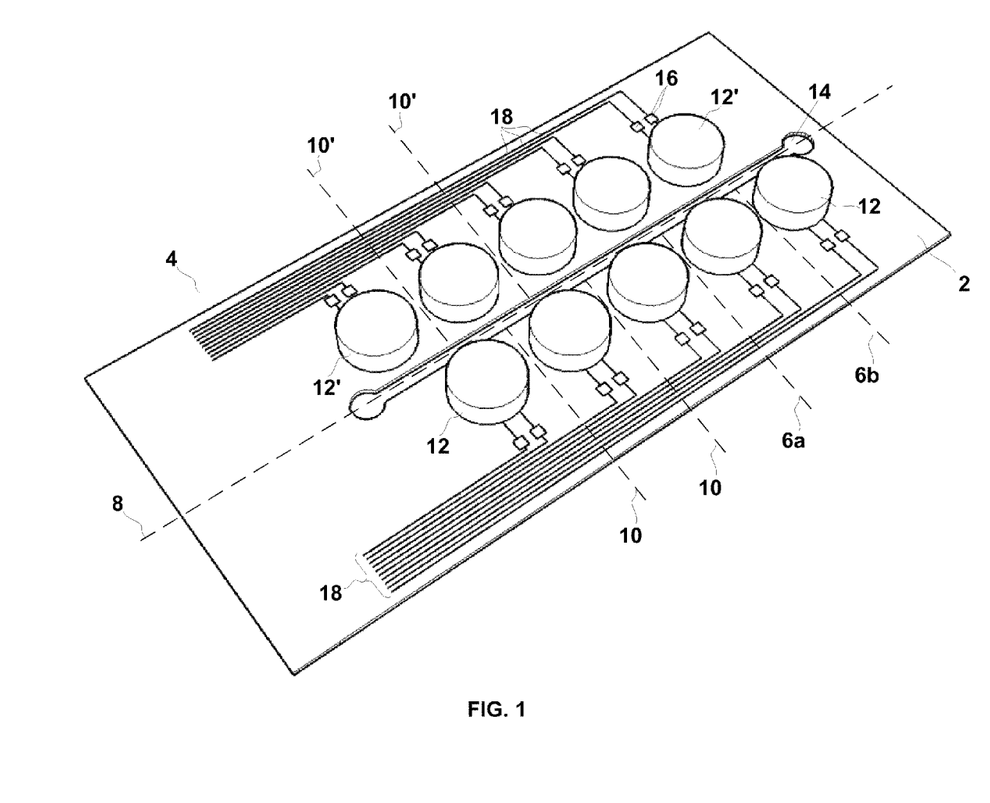
FIG. 1 is a perspective view of a flexible ECA probe of the presently disclosed preferred embodiment.

FIG. 1 illustrates a flexible ECA probe 4 of the presently disclosed preferred embodiment. The ECA probe 4 includes a base 2, which is preferably a flexible printed circuit board (PCB). Two rows of coils 12 and 12' are attached to base 2 by any coupling means such as soldering and gluing. Each row of the coils 12 and 12' are preferably parallel to each other. The middle line between rows of coils 12 and 12' defines a first bending axis 8. A cut or slit 14 is applied to base 2 along the first bending axis 8 on base 2. Preferably, there are no any other rigid objects deposited along and extending from axis 8 on base 2.

Note that slit 14 may include a circular cut at each end thereof in order to prevent tearing or the like.

It should be noted that, besides deploying a slit 14, the flexibility along axis 8 can alternatively be achieved by use of a loosely connected or flexible joint between the two sides of axis 8. The flexibility of such coupling is substantially higher than that of base 2. For example, the flexible joint could be a strip of very flexible material or a hinge means. The hinge may be fabricated using a broad range of materials, mechanisms, or a combination of the two.

As a result, base 2 can now be easily bent along axis 8, in the direction of rows of coils 12 and 12'.

Continuing with FIG. 1, turning now to the flexibility issue along bending lines transverse to rows of coils, conventionally two rows of coils 12 and 12' are arranged in staggered relationship with each other to achieve optimized coverage of the scan path and therefore high test resolution. This in which the rows of coils are arranged is adopted in presently disclosed invention. As a result, the center of each coil in row 12 and the center of each coil in row 12' does not line up with each other. As can be seen in FIG. 1, the natural bending lines, such as 10s for row 12 run right into the rigid coils of 12'. Since here the rows 12 and 12' are separated by either slit or other flexible joint 14, row 12 and 12' can now bend along their own the natural bending lines 10s or 10's separately.

It is worth noting that natural bending lines 10s and 10's do not need to be perfectly perpendicular to axis 8. Each row of coils 12s and 12's can bend in their own fashions within their own degree of freedom allowed by the space between each two coils within a row 12 or 12'. In addition, each of natural bending lines such as 6a and 6b do not have to absolutely parallel, nor have they to be in the same planer space. The inventive approach herein disclosed allows the probe to conform into 3-D shapes to the largest degree of freedom allowed by space between two coils of 12 or two coils of 12'.

It is further worth noting that separating rows 12 and 12' substantially reduces and relieves the stress force caused by non-uniform bending between adjacent rows of coils, such as 12 and 12'. As a result, deformation and undesirable shortening of probe life is substantially reduced.

Further continuing with FIG. 1, base 2 may further include bond pads 16. Each coil of 12 and 12' is electrically coupled to corresponding bond pads 16 by wire soldering or the like manner. Each bond pad 16 is electrically connected to a respective conductive trace 18. Each conductive trace may be connectable to a cable or the like for communication with an ECA system later shown in FIG. 6.

Figure 2A:
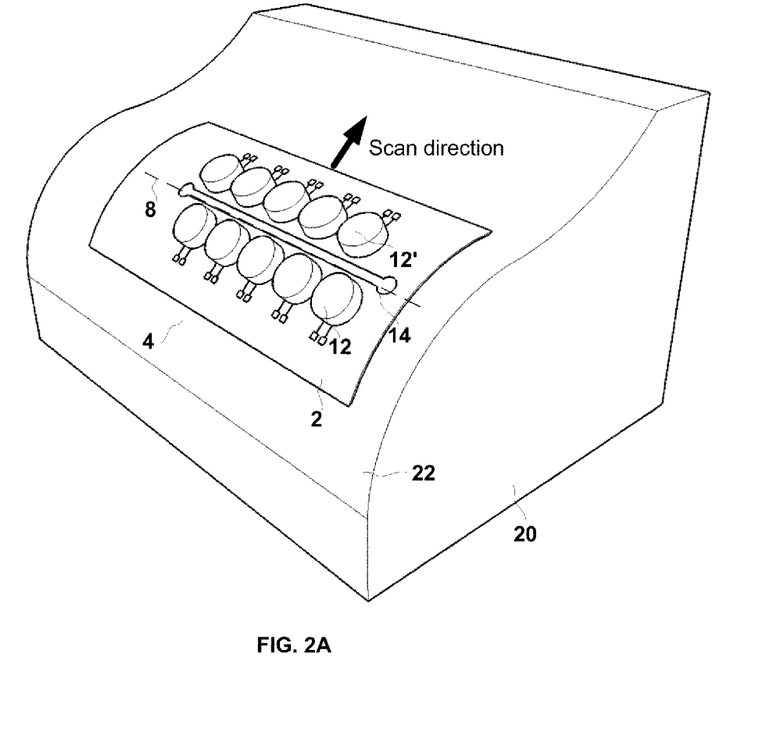
FIG. 2A shows one exemplary way of how the flexible ECA probe is used, when the probe base is bent along its bending axis.

Turning now to FIG. 2A, one exemplary way of how the flexible ECA probe is used in an ECA operation is illustrated. In this case, probe 4 is shown being used to scan test object 20 with a contoured surface 22 curving in the scan direction. Slit or flexible joint 14 allows the probe to bend in the scan direction to easily fit the contoured surface.

Figure 2B:
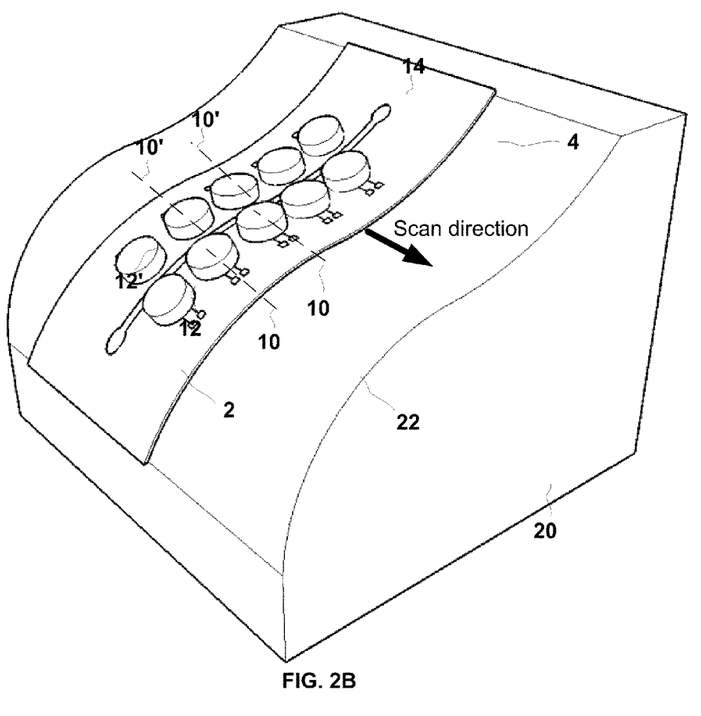
FIG. 2B shows another exemplary way of how the flexible ECA probe is used, when the probe base is bent along bending axes extending roughly perpendicular to the direction of coil rows.

FIG. 2B shows another exemplary way of how the flexible ECA probe is used in another ECA operation. In this case, probe 4 is shown being used to scan test object 20 with a contoured surface 22 curving in direction transverse to scan direction. Slit or flexible joint 14 allows base 2 bend along natural bending lines 10 and 10' without causing undesirable deformation to base 2

Figure 3:
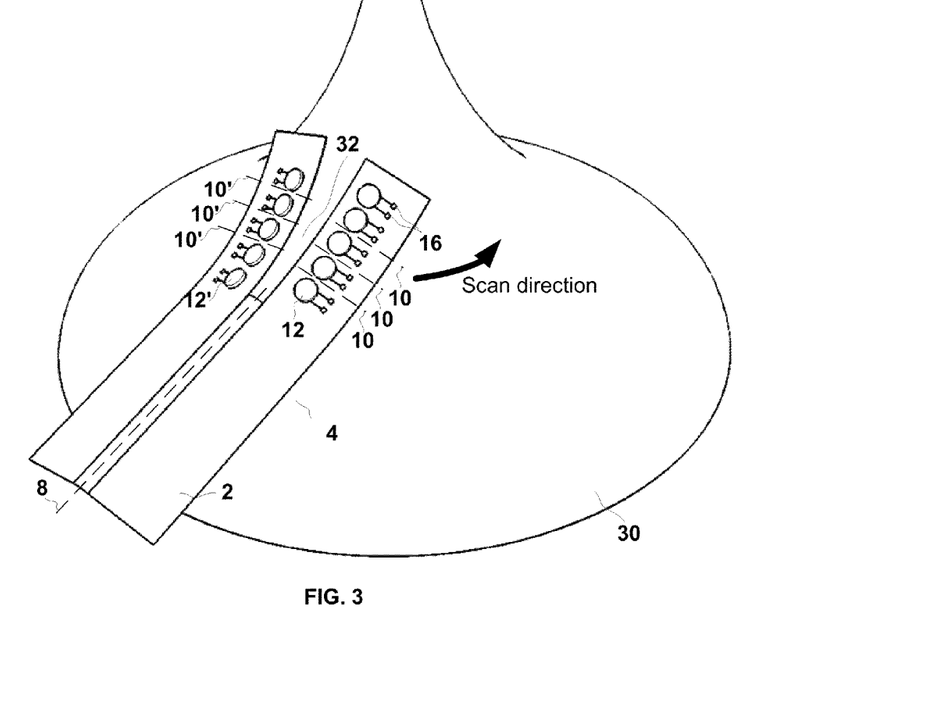
FIG. 3 shows another exemplary way of how the flexible ECA probe is used, when the probe base is bent along the rows of coils and along the directions roughly perpendicular to the rows of coils at the same time to scan a 3D surface.

FIG. 3 shows another exemplary way of how the flexible ECA probe 4 is used. Cut 32 is applied along axis 8. Probe base 2 is bent along the rows of coils (direction of axis 8) and along the natural bending lines of 10s and 10's. Note that due to cut 32, natural bending lines of 10s and 10's can each be in any direction allowed by the freedom of space provided between two adjacent coils and they do not have to be parallel to each other, nor have they to be in the same plainer space. 10s and 10's can be roughly perpendicular to axis 8. A test object 30 with complicated contour surface as shown in FIG. 3 can therefore be scanned with intimate fit by the inventive probe 4.

Also should be noted in FIG. 3 is that slit or flexible joint 14 in previous figures can be applied through the edge of base 2 as shown by slit or joint 32. The slit or flexible joint in this case may alternatively be simply an opening 32.

Figure 4:
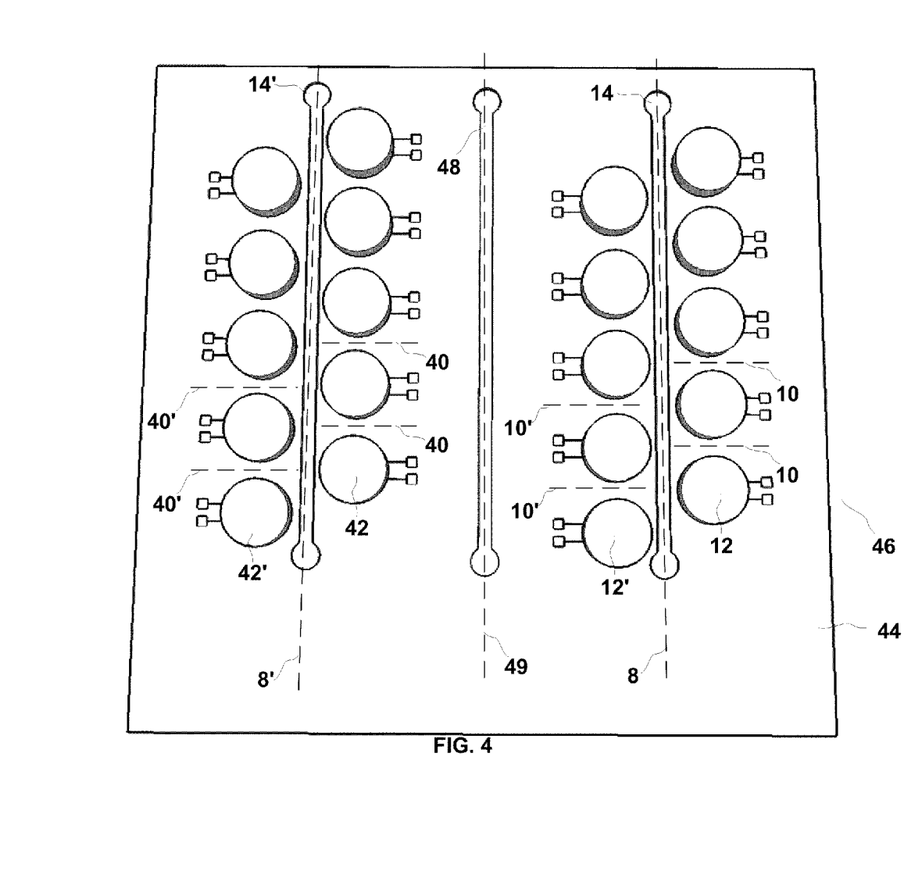
FIG. 4 is a planner view of an alternative embodiment wherein more than two rows of coils are used wherein the probe can be bent along the rows of coils and along directions roughly perpendicular to the rows of coils at the same time to increase the inspection resolution when scanning a 3D surface.

FIG. 4 is a planner view of an alternative embodiment wherein probe 46 has more than two rows of coils, 12, 12', 42 and 42' attached to base 44. With this design, the offset of the centers of adjacent coils would be 25% compared to that of 50% for two-row-coil design as aforementioned. As a result, higher test resolution can be achieved. Similarly, slits or flexible joints 14, 14' are applied along the middle line between the two rows of coils 12, 12' and 42 and 42', respectively. Another slit or flexible joint 48 is applied in parallel to and along the middle line between rows 42 and 12'. Base 44 can therefore be bent along directions of the rows of coils, along axes 8, 8', and 49. Also since base 44 under row of coils 12, 12' and 42 and 42' are separated by either slit or other flexible joint 14, 14' and 48, base 44, each strip of base 44 can now bend along their own natural bending lines 10s, 10's, 40s and 40's separately.

Similarly, the bending along natural bending lines 10s, 10's, 40s and 40's can be roughly perpendicular to the direction of rows of coils. The natural bending lines 10s, 10's, 40s and 40's are not fixed and have certain degree of freedom allowed by the space between two adjacent coils.

Also similarly, it is further worth to mention that discontinuing the non-uniform deformation along lines 10 and 10', 40s and 40's substantially reduces and relieves the stress force caused by non-uniform bending between adjacent rows of coils, such as 12 and 12'. As a result, deformation and undesirable shortening of probe life is substantially reduced.

As a result, probe 46 can be conformed to achieve an intimate fit with a 3D surface of a test object when being moved across the 3D surface, while maintaining a high inspection resolution by staggering the rows of coils.

Figure 5:
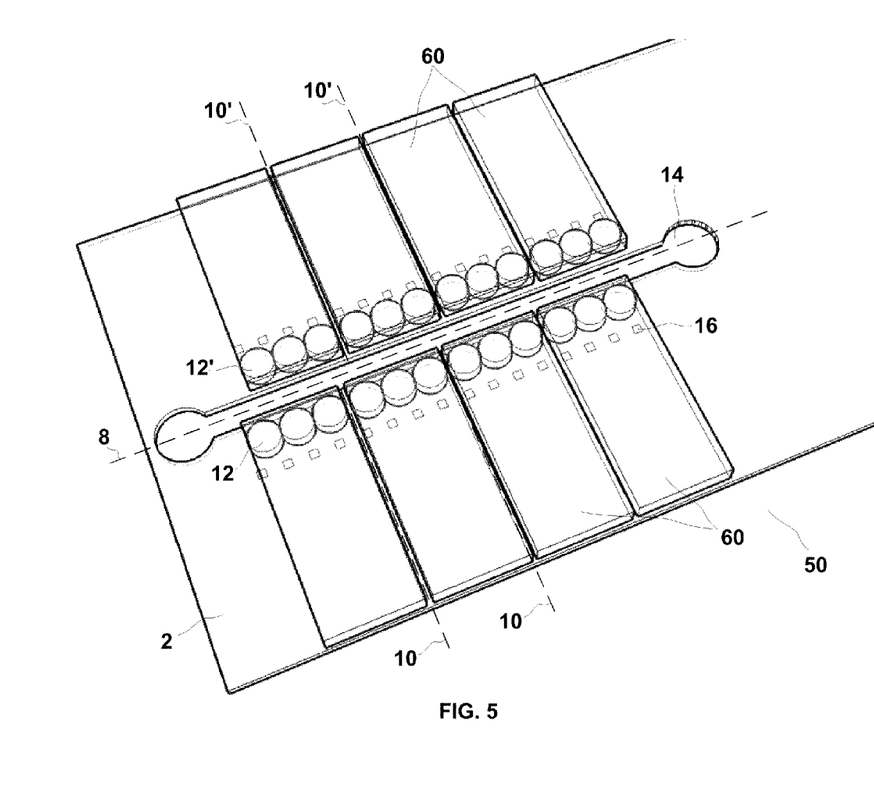
FIG. 5 is a perspective view of yet another alternative embodiment wherein support blocks are used.

Referring now to FIG. 5, in another alternative embodiment of the present invention, to protect coils 12, 12', support blocks 60 are added on top of probe 50. In one design for support blocks 60, polyurethane can be directly molded on top of coils 12 and 12', bond pads 16 and base 2. Noting that slit or flexible joint 14 is applied along axis 8 similarly to preferred embodiment, probe 50 can be bent freely along axis 8. In order to maintain desired flexibility of the probe, support blocks 60 can be designed to cover a few, such as three, coils 12 at a time, leaving natural bending lines 10s and 10's open. Using removable attaching means, support blocks 60 can also be fabricated separately from probe 50, prior to being placed onto the probe, each covering several coils of 12 and 12', bond pads 16 and a portion of base 2. In this way, support blocks 60 can be removed when it is needed to increase the flexibility of probe 50. In addition, each block 60 is spaced from an adjacent block. The spacing of blocks 60 allows for natural bending lines 10 and 10' between blocks 60. Moreover, support blocks 60 may prevent bending at coil locations, and are rigid enough to allow direct pressing over coils 12, 12'.

It should be appreciated that as constant distance between coil and test object is a very important aspect of ECA nondestructive testing, the ability to apply pressure directly behind the coils is an advantage obtained when support blocks 60 are used. Support blocks 60 allow application of back pressure directly at coil locations, thereby improving inspection resolution and service life of the probe. It is more advantageous when very small coils (e.g. 1 mm diameter) are used in ECA probe since small coils are more fragile.

It should be appreciated that having multiple coils under a support block 60 allows for the connection of multiple coils to a common pad, such as a common bond pad.

Figure 6:
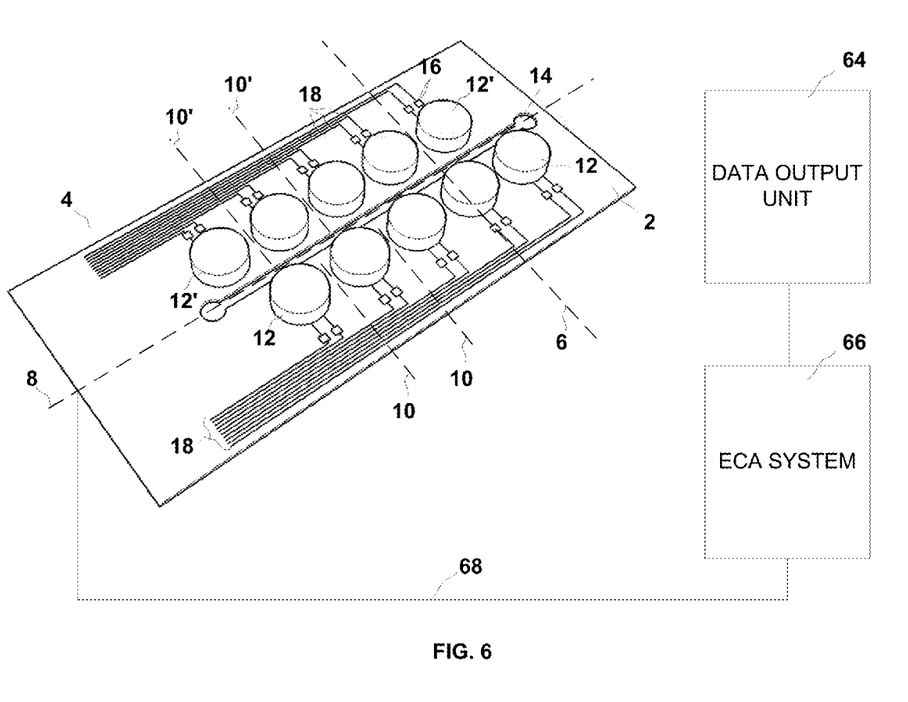
FIG. 6 is a schematic view showing disclosed flexible probe 4 used in an ECA system.

Illustrated in FIG. 6 is when the presently disclosed flexible probe 4 is used in an ECA system 66. Test data collected from probe 4 is transmitted through data cable 68 to ECA system 66. After test data is analyzed by system 66, graphical or text representing test result is provided via a data output unit 64 such as a display screen.

Although the present invention has been described in relation to particular exemplary embodiments thereof, many other variations and modifications and other uses will become apparent to those skilled in the art. It is preferred, therefore, that the present invention not be limited by the specific disclosure. For example, the scope of the present disclosure may be applied to a wide range of probes such as, but not limited to Ultrasonic (UT) single element, multi-element, and array probes.

What is claimed is:

1. A flexible array probe suitable for being conformed to test surfaces of contoured three-dimensional objects, the array probe comprising:
   a plurality of sensing elements;
   a base formed of a flexible material, the base having a surface for being placed against and/or moved across the test surfaces;
   the flexible base having a first direction and at least one linear bending region extending substantially along the first direction, the bending region being fanned so that deformation in the material of the base on a first side of the bending region are substantially prevented from being transmitted to a second side of the base, across the bending region, wherein the bending region includes at least one longitudinal cut in the base along the first direction;
   wherein the base is constructed to be bent along the first direction and along bending axes which extend at angles relative to the first direction; and
   the sensing elements being fastened onto the base straddling the at least one bending region.

2. The array probe of claim 1, in which the sensing elements are constructed as coil elements.

3. The array probe of claim 2, wherein the coil elements are arranged in a matrix.

4. The array probe of claim 1, in which the sensing elements are arranged in rows of elements substantially parallel to the first direction.

5. The array probe of claim 4, in which the one row of elements is arranged in staggered relationship with the adjacent row of elements.

6. The array probe of claim 1, wherein the bending axes on the first side of the base can be in different angles relative to the bending axes on the second side of the base.

7. The array probe of claim 1, including electrical wiring for connecting to the sensing elements and the electrical wiring being formed on the base.

8. The array probe of claim 7, in which the electrical wiring extends at least in part perpendicularly to the at least one bending region.

9. The array probe of claim 1, including circular cuts at distal ends of each one of the at least one cut.

10. The array probe of claim 1, wherein the cut in the base forms the bending region as a flexible joint, so that the material of the base is substantially more flexible at the bending region than the material of the base at other regions of the base.

11. The array probe of claim 1, wherein the base is formed as a printed circuit board (PCB).

12. The array probe of claim 11, wherein the array probe comprises bonding pads for the sensing coils.

13. The array probe of claim 1, further comprising support structure which is configured to protect the coil elements.

14. The array probe of claim 13, wherein the support structure is formed of cast polyurethane.

15. The array probe of claim 13, wherein the support structure provides bending means along the bending axes.

16. The array probe of claim 1, in combination with a data acquisition and processing module and the array probe being connected to the acquisition and processing module by a cable.

17. The array probe of claim 1, wherein the bending region includes at least one longitudinal stripe of flexible material connected to the base.

* * * * *